US012716826B2

(12) United States Patent
Oishi

(10) Patent No.: US 12,716,826 B2
(45) Date of Patent: Aug. 25, 2026

(54) ANALYSIS METHOD

(71) Applicant: SUMITOMO RUBBER INDUSTRIES, LTD., Kobe (JP)

(72) Inventor: Kentaro Oishi, Kobe (JP)

(73) Assignee: SUMITOMO RUBBER INDUSTRIES, LTD., Kobe (JP)

( * ) Notice: Subject to any disclaimer, the term of this patent is extended or adjusted under 35 U.S.C. 154(b) by 453 days.

(21) Appl. No.: 18/109,509

(22) Filed: Feb. 14, 2023

(65) Prior Publication Data

US 2023/0280256 A1 Sep. 7, 2023

(30) Foreign Application Priority Data

Mar. 7, 2022 (JP) ................................ 2022-034453

(51) Int. Cl.
*G01N 15/06* (2024.01)
*G16C 20/20* (2019.01)

(52) U.S. Cl.
CPC ............. *G01N 15/06* (2013.01); *G16C 20/20* (2019.02)

(58) Field of Classification Search
CPC ................................ G01N 15/06; G16C 20/20
See application file for complete search history.

(56) References Cited

U.S. PATENT DOCUMENTS 4,220,042 A 9/1980 Vegvari et al.
10,858,461 B2 * 12/2020 Kida ...................... C08L 23/12
12,291,720 B2 * 5/2025 Kuwahara ............ C12N 5/0621
2023/0391984 A1 * 12/2023 Jin .......................... C08K 3/04
2024/0280512 A1 * 8/2024 Oishi .................... G01N 23/04

FOREIGN PATENT DOCUMENTS

JP S61162734 A * 7/1986
KR 10-2011-0025244 A 3/2011

* cited by examiner

*Primary Examiner* — Wyatt A Stoffa
(74) *Attorney, Agent, or Firm* — Birch, Stewart, Kolasch & Birch, LLP

(57) ABSTRACT

Provided is an analysis method enabling accurate estimation of the types, amounts, and mixing ratios of fillers present in an elastomer composition, including whether the sample contains two or more fillers. The present disclosure relates to an analysis method including estimating the type, amount, and mixing ratio of at least one filler in an elastomer composition containing an elastomer component and the filler, the method including estimation based on the property, particle size, and particle size distribution of the filler.

4 Claims, 7 Drawing Sheets

Comparison of particle size distribution

FIG.3

| Section | | GPF Mean | GPF 3σ |
|---|---|---|---|
| 0 | – | 0 | 0 |
| 5 | 0～5 | 0.4 | 1.3 |
| 10 | 5～10 | 0 | 0 |
| 15 | 10～15 | 0 | 0 |
| 20 | 15～20 | 0 | 0 |
| 25 | 20～25 | 1.4 | 2.0 |
| 30 | 25～30 | 2.5 | 2.7 |
| 35 | 30～35 | 7.3 | 4.2 |
| 40 | 35～40 | 11.9 | 5.1 |
| 45 | 40～45 | 11.3 | 5.4 |
| 50 | 45～50 | 9.8 | 4.4 |
| 55 | 50～55 | 8.0 | 4.8 |
| 60 | 55～60 | 6.7 | 4.6 |
| 65 | 60～65 | 7.9 | 4.8 |
| 70 | 65～70 | 7.3 | 4.7 |
| 75 | 70～75 | 5.9 | 3.8 |
| 80 | 75～80 | 3.9 | 3.6 |
| 85 | 80～85 | 3.2 | 2.9 |
| 90 | 85～90 | 3.4 | 3.1 |
| 95 | 90～95 | 1.9 | 1.9 |
| 100 | 95～100 | 2.5 | 2.8 |
| 105 | 100～105 | 1.7 | 2.3 |
| 110 | 105～110 | 1.0 | 1.4 |
| 115 | 110～115 | 0.3 | 1.1 |
| 120 | 115～120 | 0.3 | 0.7 |
| 125 | 120～125 | 0.4 | 1.0 |
| 130 | 125～130 | 0.4 | 1.1 |
| 135 | 130～135 | 0.3 | 0.9 |
| 140 | 135～140 | 0.1 | 0.5 |
| 145 | 140～145 | 0.2 | 0.8 |
| 150 | 145～150 | | |
| 155 | 150～155 | | |
| 160 | 155～160 | | |
| 165 | 160～165 | | |
| 170 | 165～170 | | |
| 175 | 170～175 | | |
| 180 | 175～180 | | |
| 185 | 180～185 | | |
| 190 | 185～190 | | |
| 195 | 190～195 | | |
| 200 | 195～200 | | |
| | (nm) | (%) | (%) |

FIG.4

| Section | Formulation 2 | GPF 73.53 | Percentage of agreement [%] |
|---|---|---|---|
| 0 | 0 | ○ | |
| 5 | 0 | ○ | |
| 10 | 0 | ○ | |
| 15 | 3.0 | × | |
| 20 | 21.8 | × | |
| 25 | 17.1 | × | |
| 30 | 14.7 | × | |
| 35 | 10.5 | ○ | |
| 40 | 9.5 | ○ | |
| 45 | 3.0 | × | |
| 50 | 3.5 | × | |
| 55 | 2.5 | × | |
| 60 | 2.6 | ○ | |
| 65 | 2.3 | × | |
| 70 | 2.6 | ○ | |
| 75 | 1.7 | × | |
| 80 | 1.6 | ○ | |
| 85 | 1.6 | ○ | |
| 90 | 0.7 | ○ | |
| 95 | 0.5 | ○ | |
| 100 | 0.4 | ○ | |
| 105 | 0.3 | ○ | |
| 110 | 0.1 | ○ | |
| 115 | 0.2 | ○ | |
| 120 | 0 | ○ | |
| 125 | 0 | ○ | |
| 130 | 0.1 | ○ | |
| 135 | 0 | ○ | |
| 140 | 0 | ○ | |
| 145 | 0 | ○ | |
| 150 | 0 | ○ | |
| 155 | 0 | ○ | |
| 160 | 0 | ○ | |
| 165 | 0 | ○ | |
| 170 | 0 | ○ | |
| 175 | 0 | ○ | |
| 180 | 0 | ○ | |
| 185 | 0 | ○ | |
| 190 | 0 | ○ | |
| 195 | 0 | ○ | |
| 200 | 0 | ○ | |

※Determination range: within ± 5 classes of the range where particles are present

FIG.5

| Section | Formulation 3 | GPF 82.35 | Percentage of agreement [%] |
|---|---|---|---|
| 0 | 0 | ○ | |
| 5 | 0 | ○ | |
| 10 | 0 | ○ | |
| 15 | 2.3 | × | |
| 20 | 16.8 | × | |
| 25 | 13.2 | × | |
| 30 | 11.4 | × | |
| 35 | 8.7 | ○ | |
| 40 | 8.9 | ○ | |
| 45 | 4.1 | × | |
| 50 | 4.5 | × | |
| 55 | 4.9 | ○ | |
| 60 | 3.9 | ○ | |
| 65 | 4.2 | ○ | |
| 70 | 4.3 | ○ | |
| 75 | 3.7 | ○ | |
| 80 | 3.2 | ○ | |
| 85 | 2.0 | ○ | |
| 90 | 1.3 | ○ | |
| 95 | 0.7 | ○ | |
| 100 | 0.9 | ○ | |
| 105 | 0.4 | ○ | |
| 110 | 0.2 | ○ | |
| 115 | 0.2 | ○ | |
| 120 | 0 | ○ | |
| 125 | 0.1 | ○ | |
| 130 | 0.1 | ○ | |
| 135 | 0 | ○ | |
| 140 | 0 | ○ | |
| 145 | 0 | ○ | |
| 150 | 0 | ○ | |
| 155 | 0 | ○ | |
| 160 | 0 | ○ | |
| 165 | 0 | ○ | |
| 170 | 0 | ○ | |
| 175 | 0 | ○ | |
| 180 | 0 | ○ | |
| 185 | 0 | ○ | |
| 190 | 0 | ○ | |
| 195 | 0 | ○ | |
| 200 | 0 | ○ | |

※Determination range: within ± 5 classes of the range where particles are present Comparison of particle size distribution Comparison of particle size distribution

ANALYSIS METHOD

TECHNICAL FIELD

The present disclosure relates to an analysis method.

BACKGROUND ART

Methods have been used for measuring the average particle size and particle size distribution of the filler dispersed in an elastomer composition containing an elastomer, a filler, and other components. However, it is desirable to accurately analyze the types, amounts, and mixing ratios of fillers, as well as whether multiple types of fillers are present or not.

SUMMARY OF DISCLOSURE

Technical Problem

The present disclosure aims to solve the above problem and provide an analysis method enabling accurate estimation of the types, amounts, and mixing ratios of fillers present in an elastomer composition, including whether the sample contains two or more fillers.

Solution to Problem

The present disclosure relates to an analysis method, including estimating the type, amount, and mixing ratio of at least one filler in an elastomer composition containing an elastomer component and the filler, the method including estimation based on the property, particle size, and particle size distribution of the filler.

Advantageous Effects of Disclosure

According to the present disclosure, an analysis method is provided which includes estimating the type, amount, and mixing ratio of at least one filler in an elastomer composition containing an elastomer component and the filler, and which includes estimation based on the property, particle size, and particle size distribution of the filler. Such a method enables accurate estimation of the types, amounts, and mixing ratios of fillers present in an elastomer composition, including whether the sample contains two or more fillers.

BRIEF DESCRIPTION OF DRAWINGS

FIG. 3 shows exemplary data of mean particle size distributions and 3σ values of a standard filler (carbon black SAF, ISAF, HAF, FEF, GPF), and the lower control limits (LCL) and upper control limits (UCL) obtained from the means and 3σ values.

FIG. 4 shows exemplary results of comparative analysis between the particle size distribution of the filler (carbon black) in the sample of Formulation 2 and the particle size distribution of a standard filler (SAF, ISAF, HAF, FEF, GPF).

FIG. 5 shows exemplary results of comparative analysis between the particle size distribution of the filler (carbon black) in the sample of Formulation 3 and the particle size distribution of a standard filler (SAF, ISAF, HAF, FEF, GPF).

DESCRIPTION OF EMBODIMENTS

Figure 1:
FIG. 1 shows an exemplary particle size distribution of carbon black (filler to be analyzed) present in a sample of Formulation 2.
Figure 1:
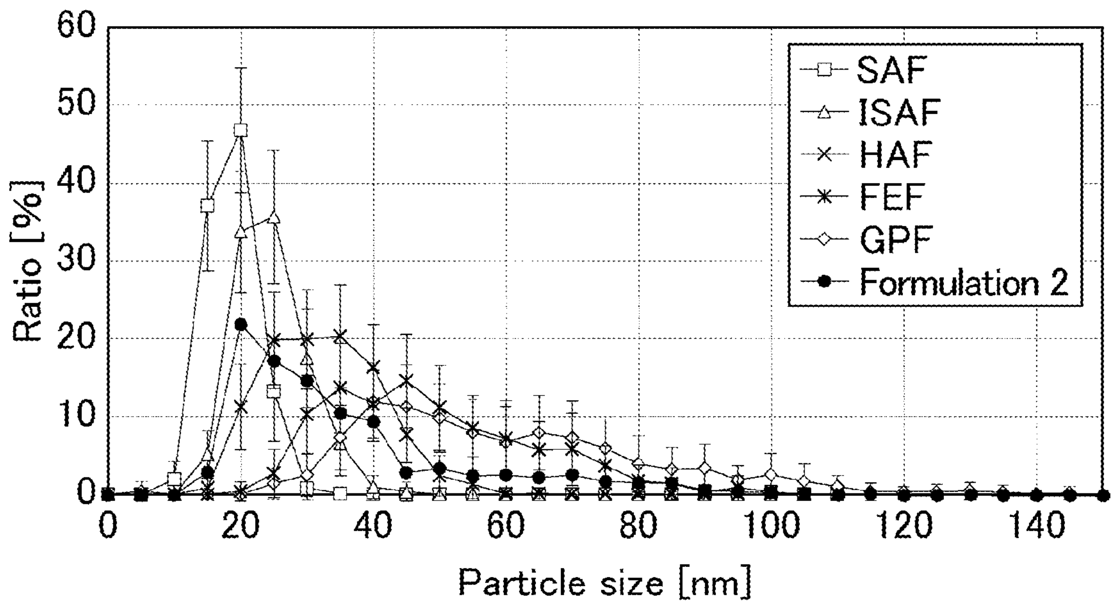

The present disclosure relates to an analysis method which includes estimating the type, amount, and mixing ratio of at least one filler in an elastomer composition containing the filler and an elastomer, and which includes estimation based on the property, particle size, and particle size distribution of the filler.

The method of the present disclosure makes analysis based on the results of measurements of the property, particle size, and particle size distribution of a filler dispersed in an elastomer composition, and thus can determine which commercial product (standard product) the filler in the composition has a primary particle size equivalent to.

Moreover, since the method measures the particle size and particle size distribution of the filler in the composition, for example, the measured particle size and particle size distribution may be compared with the particle size and particle size distribution of a commercial product (standard product) to determine whether two or more fillers are present, the amount of each filler, and the mixing ratio thereof not only in a sample containing a single filler but also in a sample containing two or more fillers (e.g., two or more types of carbon black, two or more types of silica, or one or more types of carbon black and one or more types of silica).

Accordingly, the present disclosure enables estimation of the type (e.g., grade) of filler in an elastomer composition, the presence or absence of two or more fillers, the amount of each filler, and the mixing ratio thereof.

In the analysis method of the present disclosure, an elastomer composition (sample) containing an elastomer component and a filler is analyzed. Any elastomer component may be used including diene rubbers. Examples of diene rubbers include isoprene-based rubbers, polybutadiene rubbers (BR), styrene-butadiene rubbers (SBR), styrene-isoprene-butadiene rubbers (SIBR), ethylene-propylene-diene rubbers (EPDM), chloroprene rubbers (CR), and acrylonitrile butadiene rubbers (NBR). Butyl-based rubbers and fluororubbers are also usable. These may be used alone or in combinations of two or more.

Any filler that is known in the rubber field can be used. Examples include inorganic fillers such as carbon black, silica, calcium carbonate, talc, alumina, clay, aluminum hydroxide, aluminum oxide, and mica, and hardly dispersible fillers. Carbon black or silica is suitable among these.

Any carbon black may be used, and examples include SAF, ISAF, HAF, FF, FEF, FEF, and GPF. Usable commercial products are available from Asahi Carbon Co., Ltd., Cabot Japan K.K., Tokai Carbon Co., Ltd., Mitsubishi Chemical Corporation, Lion Corporation, NIPPON STEEL Carbon Co., Ltd., Columbia Carbon, etc. These may be used alone or in combinations of two or more. In particular, the analysis method of the present disclosure enables estimation of the type (grade), amount, and ratio of each carbon black not only in a sample containing only one carbon black but also in a sample containing two or more types of carbon black.

In the elastomer composition (sample), the amount of carbon black is not limited and may be, for example, 1 to 150 parts by mass, preferably 3 to 100 parts by mass, more preferably 5 to 80 parts by mass, per 100 parts by mass of the elastomer component content. When the amount of carbon black is within the range indicated above, the type (grade), amount, and ratio of each carbon black in the sample tend to be accurately estimated.

Examples of silica include dry silica (anhydrous silica) and wet silica (hydrous silica). Wet silica is preferred because it has a large number of silanol groups. The material of the silica may be water glass (sodium silicate) or a biomass material such as rice husks. Usable commercial products are available from Evonik Degussa, Tosoh Silica Corporation, Solvay Japan, Tokuyama Corporation, etc. Each of these may be used alone, or two or more of these may be used in combination. In particular, the analysis method of the present disclosure enables estimation of the type (grade), amount, and ratio of each silica not only in a sample containing only one silica but also in a sample containing two or more types of silica.

In the elastomer composition (sample), the amount of silica is not limited and may be, for example, 1 to 150 parts by mass, preferably 3 to 100 parts by mass, more preferably 5 to 80 parts by mass, per 100 parts by mass of the elastomer component content. When the amount of silica is within the range indicated above, the type, amount, and ratio of each silica in the sample tend to be accurately estimated.

The analysis method of the present disclosure estimates the type, amount, and mixing ratio of at least one filler present in an elastomer composition (sample) based on the property, particle size, and particle size distribution of the filler present in the sample. The property of the filler may be, for example, the shape, surface activity, structure size, or aggregate distribution of the filler.

Among these properties of the filler, the shape of the filler is desirable in order to accurately estimate the type, amount, and ratio of each filler. The filler may have any shape such as a spherical, acicular, rod, or amorphous shape.

The present disclosure relates to an analysis method including estimating the type, amount, and mixing ratio of at least one filler (carbon black, silica, etc.) in an elastomer composition (sample) based on the property, particle size, and particle size distribution of the filler. From the standpoint of accurate estimation, the method desirably includes treating the sample at a high temperature under a nitrogen atmosphere or air atmosphere, and analyzing the filler (filler in the sample) collected after the treatment.

For example, such high temperature treatment and filler collection can be performed by applying the following technique to the sample (elastomer composition).

The sample is heated up to 650° C. under a nitrogen atmosphere by thermogravimetric analysis (TGA), and the remaining component (e.g., carbon black, silica) is extracted.

The remaining component (filler to be analyzed) is sufficiently ultrasonically dispersed in a solvent (ethanol) and then dropped onto a mesh for transmission electron microscopic (TEM) observation.

Although the treatment temperature for the high temperature treatment in the above technique is 650° C., the temperature may be selected as appropriate to ensure that no elastomer component remains in the sample and that the filler to be analyzed (e.g., carbon black, silica) remains in the sample. For example, the treatment may be carried out at 500 to 800° C. Such a high temperature treatment of the sample (elastomer composition) allows the filler to be analyzed to remain and be collected.

Although in the above technique, the remaining component (e.g., carbon black, silica) is ultrasonically dispersed in a solvent, any method that can disperse the filler to be analyzed (e.g., carbon black, silica) can be selected as appropriate. Examples of the solvent include, in addition to ethanol, organic solvents such as methanol, tetrahydrofuran, and acetone, and water. Moreover, the filler can also be dispersed in the solvent by a means other than the ultrasonic treatment, such as using a high-speed homogenizer, colloid mill, or blender mill.

After the filler to be analyzed (e.g., carbon black, silica) is dropped onto a mesh for transmission electron microscopic (TEM) observation by the above technique or other techniques, for example, the following technique may be applied to the filler to analyze the property, particle size, and particle size distribution of the filler present in the sample.

TEM observation is performed on the dropped filler to be analyzed (e.g., carbon black, silica), and images are acquired at a magnification sufficient to determine the primary particle size.

The images are acquired until the number of particles reaches about 300.

The particle sizes are calculated from the acquired images to determine the particle size distribution.

As mentioned in the above technique including TEM observation of the filler to be analyzed (e.g., carbon black, silica) as an example, it is desirable to use electron microscopic observation in order to accurately estimate the property, particle size, and particle size distribution of the filler present in the sample (elastomer composition). Also usable is a scanning electron microscope (SEM).

Although in the above technique as an example, TEM observation is performed and images are acquired at a magnification sufficient to determine the primary particle size and until the number of particles reaches about 300, the magnification and the number of particles may be selected as appropriate in the electron microscopic observation. Moreover, the particle size of the filler to be analyzed can be determined by observing the filler using an electron microscope, measuring the particle sizes of at least a predetermined number of fillers observed in the field of view, and averaging the measured particle sizes. Although the number of particles is about 300 in the present case, the number of particles is not limited thereto and may be selected as appropriate in consideration of the accuracy of measurement or other factors.

Thus, the particle sizes can be determined from the acquired images, and the particle size distribution can be calculated from the particle sizes.

Here, the particle size can be, for example, the spherical diameter when the filler has a spherical shape, the minor axis when the filler has an acicular or rod shape, or the average diameter from the center when the filler has an amorphous shape.

The analysis method of the present disclosure estimates the type, amount, and mixing ratio of the filler to be analyzed, based on the property, particle size, and particle size distribution of the filler determined by the above technique or other techniques. From the standpoint of accurate estimation, the method desirably includes estimation based on a comparison between the shape, particle size, and particle size distribution of the filler present in the sample (elastomer composition) and the shape, particle size, and particle size distribution of a standard filler obtained separately.

An exemplary method of such estimation is described below, but the analysis method of the present disclosure is not limited to the following method.

A sample of Formulation 2 (sample prepared by kneading 66 parts by mass of ISAF, 33 parts by mass of GPF, and 100 parts by mass of a diene rubber) and a sample of Formulation 3 (sample prepared by kneading 50 parts by mass of ISAF, 50 parts by mass of GPF, and 100 parts by mass of a diene rubber), which are described later in EXAMPLES, are prepared and then subjected to high temperature treatment of the samples, collection of the fillers (carbon black) to be analyzed, electron microscopic observation, acquisition of images, and calculation of the particle size and particle size distribution according to the above techniques.

Figure 2:
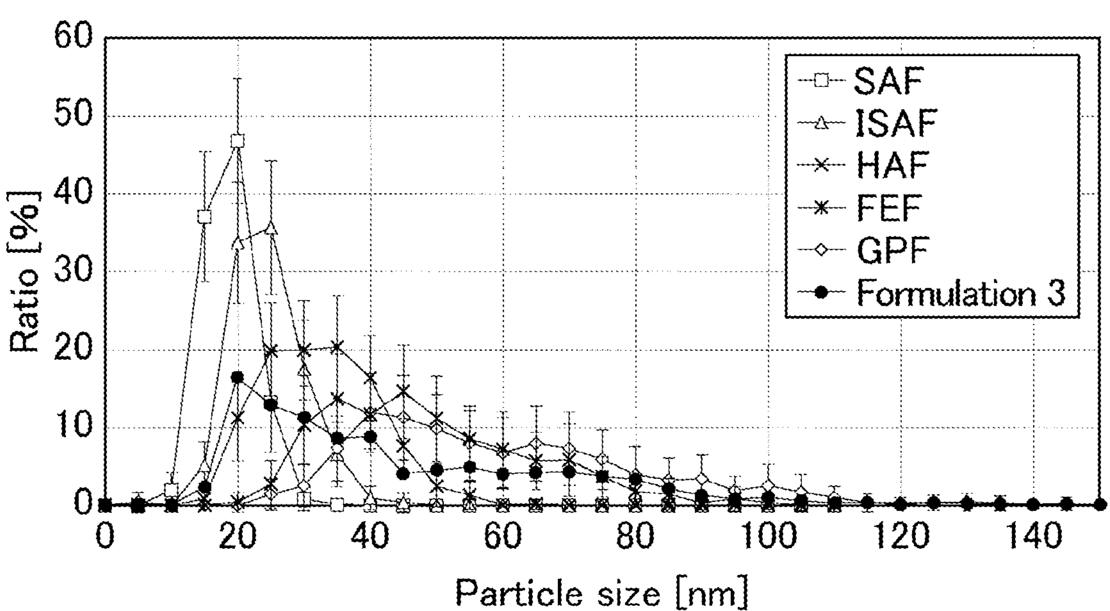
FIG. 2 shows an exemplary particle size distribution of carbon black (filler to be analyzed) present in a sample of Formulation 3.

With respect to the determined particle sizes and particle size distributions, FIG. 1 shows the particle size distribution of the carbon black (fillers to be analyzed) present in the sample of Formulation 2, and FIG. 2 shows the particle size distribution of the carbon black (fillers to be analyzed) present in the sample of Formulation 3.

FIG. 3 shows the mean particle size distributions and 3σ values of a standard filler (GPF), among standard fillers (SAF, ISAF, HAF, FEF, GPF), and the lower control limits (LCL) and upper control limits (UCL) obtained from the means and 3σ values. FIGS. 1 and 2 also show graphs of these standard fillers illustrating the mean particle size distributions, LCLs, and UCLs of these standard fillers. The average particle sizes and particle size distributions of the standard fillers can be measured by conventionally known methods. Although five types of carbon black are exemplified here as the standard fillers, the standard fillers are not limited and may be any commercial filler (e.g., other types of carbon black or silica).

Here, the particle size distribution of each standard filler may be determined from about 300 particles per image (or per field of view). Further, such processing may be performed on multiple images (or multiple fields of view) to determine the mean particle size distribution, which may then be divided into sections to determine the probability of existence of the particle in each section. The 3σ value may be determined from the variations between the multiple images (or multiple fields of view).

Then, comparative analysis between the particle size distribution of the sample of Formulation 2 in FIG. 1 or the particle size distribution of the sample of Formulation 3 in FIG. 2 and the particle size distributions of the standard fillers (SAF, ISAF, HAF, FEF, GPF) may be performed to determine the type of carbon black contained in the sample of Formulation 2 or the sample of Formulation 3 (which of SAF, ISAF, HAF, FEF, and GPF is present), the amount of the carbon black, and the ratio between two or more types of carbon black, if present.

In particular, from the standpoint of accurate estimation, a comparison between the shape, particle size, and particle size distribution of the filler present in the sample and the shape, particle size, and particle size distribution of a standard filler obtained separately is desirably performed based on, for example, the percentage of agreement between the particle size distribution of the filler and the particle size distribution of the standard filler.

FIG. 4 shows the results of comparative analysis between the particle size distribution of the fillers (carbon black) in the sample of Formulation 2 and the particle size distribution of GPF as an example, among the standard fillers (SAF, ISAF, HAF, FEF, GPF).

Similarly, FIG. 5 shows the results of comparative analysis between the particle size distribution of the fillers (carbon black) in the sample of Formulation 3 and the particle size distribution of GPF as an example, among the standard fillers (SAF, ISAF, HAF, FEF, GPF).

Here, if the ratio (%) of carbon black having a particle size within a predetermined range (5-nm increment in FIGS. 4 and 5) in the sample falls within the range of LCL to UCL of the standard filler within that range, "○ (agree)" is displayed, while if the ratio is outside the range, "x (disagree)" is displayed.

First, with respect to the sample of Formulation 2 in FIG. 4, the ratio of carbon black having a particle size of more than 35 nm but not more than 40 nm (section 40) in the sample is 9.5%, which is within the range of LCL (6.8%) to UCL (16.9%) of GPF having a particle size of more than 35 nm but not more than 40 nm (section 40) in FIG. 3 and therefore is marked "○".

Moreover, the ratio of carbon black having a particle size of more than 40 nm but not more than 45 nm (section 45) in the sample of Formulation 2 in FIG. 4 is 2.9%, which is outside the range of LCL (5.9%) to UCL (16.7%) of GPF having a particle size of more than 40 nm but not more than nm (section 45) in FIG. 3 and therefore is marked "x".

Then, the particle size ranges that GPF is considered to have may be selected as appropriate to calculate the percentage (%) of "○" within these ranges, which may be used as an example of the percentage of agreement with GPF (the percentage of agreement between the particle size distribution of the filler and the particle size distribution of GPF (standard filler)).

For example, for the sample of Formulation 2, the percentage of "○ (agree)" with respect to GPF within a particle size range of more than 0 nm but not more than 170 nm (sections 5 to 170) is 73.5% (=25 (the number of "○" marks)/34×100), and thus the percentage of agreement can be determined as 73.5%.

The percentages of agreement with other standard fillers (SAF, ISAF, HAF, FEF) can be calculated in the same manner. The calculation shows that the percentage of agreement with ISAF is high.

Here, for example, the number of peaks in the particle size distribution curve of the sample of Formulation 2 can be estimated as the number of types of fillers contained in the sample. Moreover, the sample can be estimated to contain fillers each having a high percentage of agreement with a standard filler.

For the sample of Formulation 2 in FIG. 1, the number of peaks in the particle size distribution curve is two and, as mentioned above, the percentage of agreement with GPF and the percentage of agreement with ISAF are high.

Accordingly, it can be estimated that the sample of Formulation 2 is likely to contain two types of carbon black, including GPF and ISAF.

Next, with respect to the sample of Formulation 3 in FIG. 5, the ratio of carbon black having a particle size of more than 35 nm but not more than 40 nm (section 40) is 8.9%, which is within the range of LCL (6.8%) to UCL (16.9%) of GPF having a particle size of more than 35 nm but not more than 40 nm (section 40) in FIG. 3 and therefore is marked "○".

Moreover, the ratio of carbon black having a particle size of more than 40 nm but not more than 45 nm (section 45) in the sample of Formulation 3 in FIG. 5 is 4.1%, which is outside the range of LCL (5.9%) to UCL (16.7%) of GPF having a particle size of more than 40 nm but not more than nm (section 45) in FIG. 3 and therefore is marked "x".

Then, the particle size ranges that the GPF is considered to have may be selected as appropriate to calculate the percentage (%) of "0" within these ranges, which may be used as an example of the percentage of agreement with GPF (the percentage of agreement between the particle size distribution of the filler and the particle size distribution of GPF (standard filler)).

For example, for the sample of Formulation 3, the percentage of "○ (agree)" with respect to GPF within a particle size range of more than 0 nm but not more than 170 nm (sections 5 to 170) is 82.3% (=28 (the number of "○" marks)/34×100), and thus the percentage of agreement can be determined as 82.3%.

The percentages of agreement with other standard fillers (SAF, ISAF, HAF, FEF) can be calculated in the same manner. The calculation shows that the percentage of agreement with ISAF is high.

Here, for example, the number of peaks in the particle size distribution curve of the sample of Formulation 3 can be estimated as the number of types of fillers contained in the sample. Moreover, the sample can be estimated to contain fillers each having a high percentage of agreement with a standard filler.

For the sample of Formulation 3 in FIG. 2, the number of peaks in the particle size distribution curve is two and, as mentioned above, the percentage of agreement with GPF and the percentage of agreement with ISAF are high.

Accordingly, it can be estimated that the sample of Formulation 3 is likely to contain two types of carbon black, including GPF and ISAF.

Moreover, the particle size distributions of the two or more standard fillers estimated to be contained in the sample may be scaled up or down as appropriate and combined to match the particle size distribution of the sample, whereby the ratio between the two or more fillers contained in the sample can be calculated. For the sample in FIG. 1, the particle size distribution of GPF and the particle size distribution of ISAF may be scaled up or down and combined to match the particle size distribution of the sample, whereby the ratio between GPF and ISAF can be calculated.

Furthermore, the amount of each of the two or more fillers estimated to be contained in the sample may be calculated by comparing the peak height and peak area of the particle size distribution of each filler with those of the particle size distribution of the corresponding standard filler. In FIG. 1, the amounts of GPF and ISAF contained in the sample may be calculated by comparing the peak height and peak area of the particle size distribution of GPF contained in the sample with those of the particle size distribution of GPF as a standard filler, and comparing the peak height and peak area of the particle size distribution of ISAF contained in the sample with those of the particle size distribution of ISAF as a standard filler.

Thus, the types, amounts, and mixing ratios of the two or more fillers contained in the sample (elastomer composition) can be estimated by such a technique, for example.

Although the examples of FIGS. 1 and 2 each show a particle size distribution curve with particle size (nm) on the X-axis and ratio (%) on the Y-axis, distribution curves constructed using other properties, such as area, can also be used.

Moreover, although, as described above, FIGS. 1 to 4 illustrate a technique for determining the percentage of agreement between the particle size distribution of the filler contained in the sample and the particle size distribution of a standard filler, any method that can determine proximity between the particle size distribution of the filler contained in the sample and the particle size distribution of a standard filler can be used, and the thus determined proximity can also be used as the percentage of agreement.

Here, the percentage of agreement between the particle size distribution of the filler contained in the sample and the particle size distribution of a standard filler can be determined by known methods. Moreover, the determination of the percentage of agreement can be automated by a means such as robotic process automation (RPA), Excel macros, or python.

Moreover, in the above-described technique, as the number of multiple images (or multiple fields of view) is small, what type of filler is present is estimated by determining the percentage of agreement. However, a clean particle size distribution curve can be obtained by increasing the number of data for each standard filler to reduce variations within each section, while changing the width of each section from 5 nm to, for example, 2.5 nm or 1 nm.

Clean particle size distribution curves of the samples of Formulations 2 and 3 can also be similarly obtained by increasing the number of images (or fields of view) to reduce variations.

Then, each particle size distribution curve may be fitted, and the fitted curve of each sample as is or after being subjected to waveform separation may be compared with the fitted curve of a standard filler to determine the type and ratio of the filler contained in the sample. This enables more accurate analysis.

Furthermore, AI or machine learning may be employed for acquisition or comparison of data.

The method described above enables estimation of the type, amount, and mixing ratio of each filler not only in a sample containing a single filler but also in a sample containing two or more fillers, based on the property (e.g., shape), particle size, and particle size distribution of the filler.

EXAMPLES

The present disclosure will be specifically described based on examples, but the disclosure is not limited only to these examples.

Preparation of Sample (Example)

First, a diene rubber and two types of carbon black according to the mixing ratio between the two types of carbon black shown in Table 1 below were introduced into a 1.7 L Banbury mixer and kneaded for three minutes at 150° C. Thus, samples (elastomer compositions) of Formulations 1 to 7 were prepared.

Each sample (elastomer composition) was subjected to high temperature treatment of the sample, collection of the carbon black to be analyzed, electron microscopic observation, acquisition of images, and calculation of the particle size and particle size distribution according to the above-described techniques. Thus, the particle size distributions of carbon black present in the samples of Formulation 1 in FIG.

Figure 7:
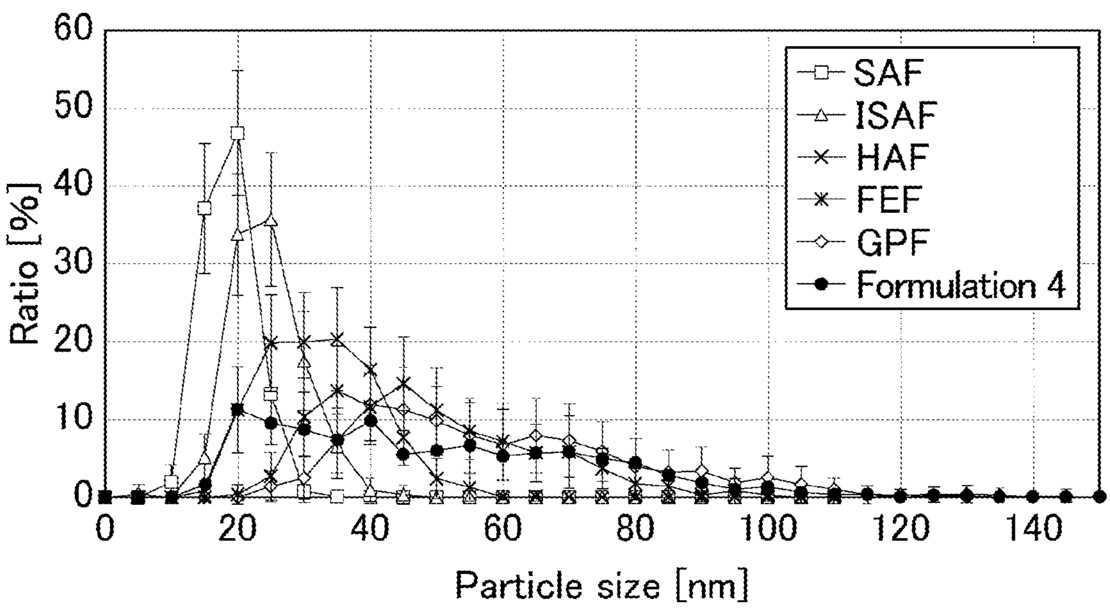
FIG. 7 shows an exemplary particle size distribution of carbon black (filler to be analyzed) present in a sample of Formulation 4.
Figure 8:
FIG. 8 shows an exemplary particle size distribution of carbon black (filler to be analyzed) present in a sample of Formulation 5.
Figure 8:
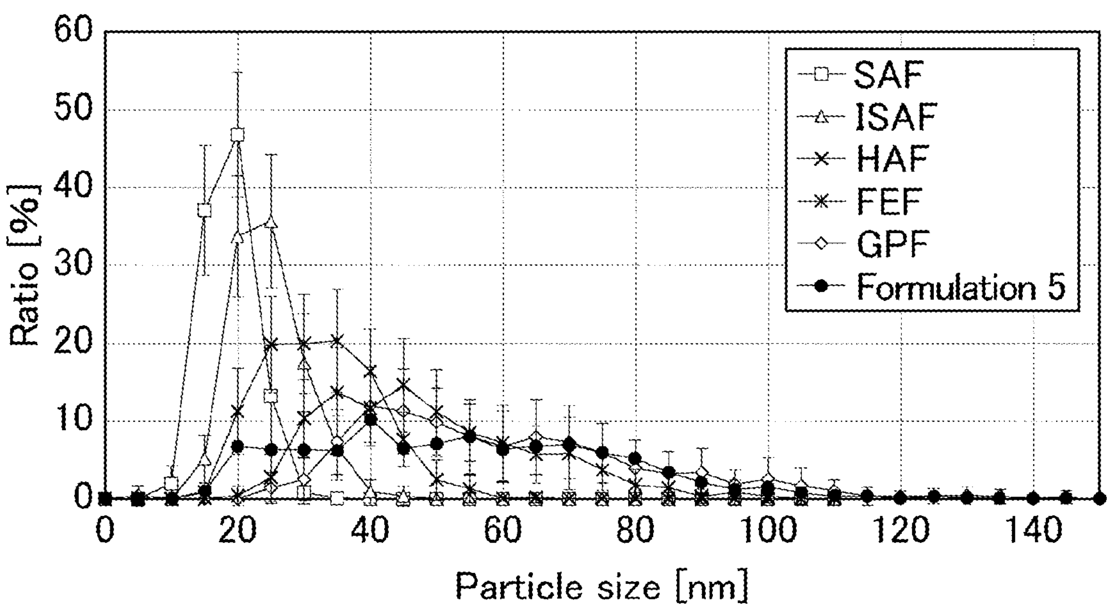
Figure 9:
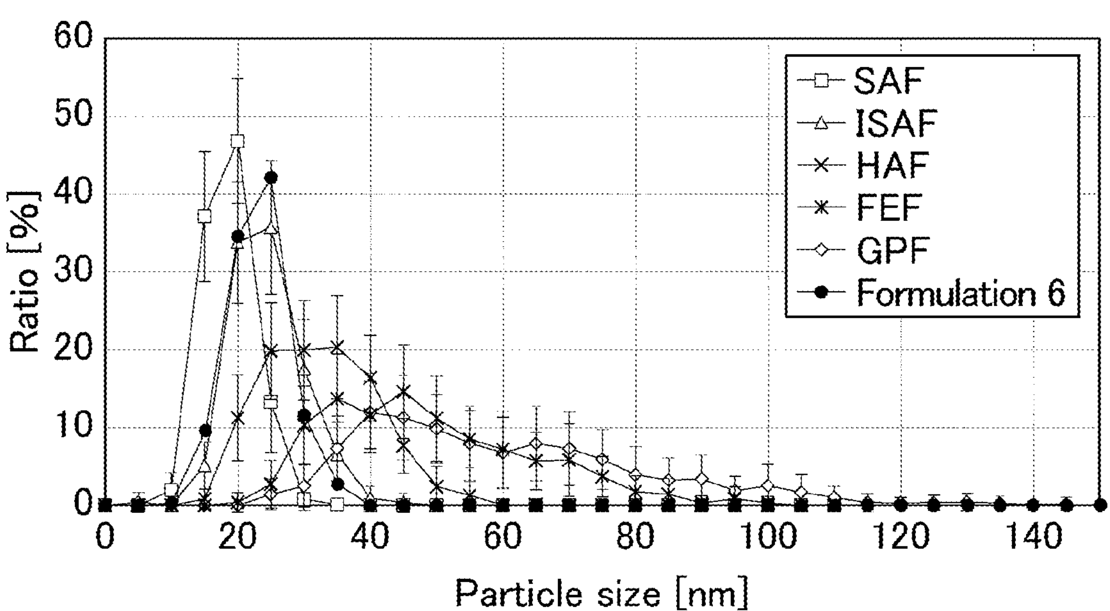
FIG. 9 shows an exemplary particle size distribution of carbon black (filler to be analyzed) present in a sample of Formulation 6.
Figure 10:
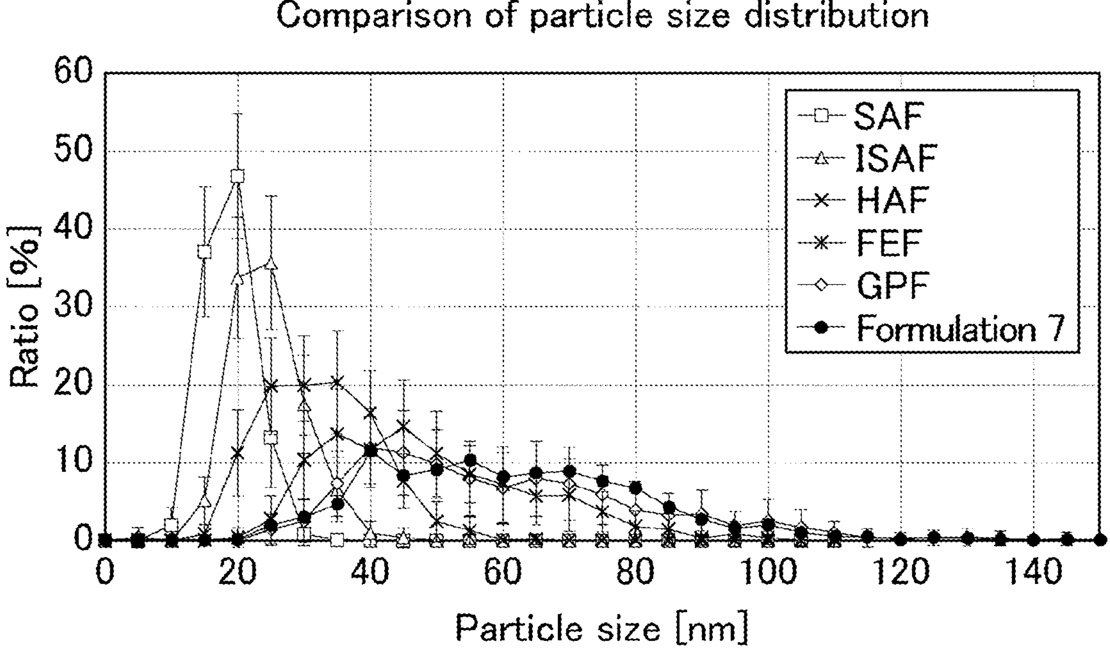
FIG. 10 shows an exemplary particle size distribution of carbon black (filler to be analyzed) present in a sample of Formulation 7.

6, Formulation 2 in FIG. 1, Formulation 3 in FIG. 2, Formulation 4 in FIG. 7, Formulation 5 in FIG. 8, Formulation 6 in FIG. 9, and Formulation 7 in FIG. 10 were obtained.

Figure 6:
FIG. 6 shows an exemplary particle size distribution of carbon black (filler to be analyzed) present in a sample of Formulation 1.
Figure 6:
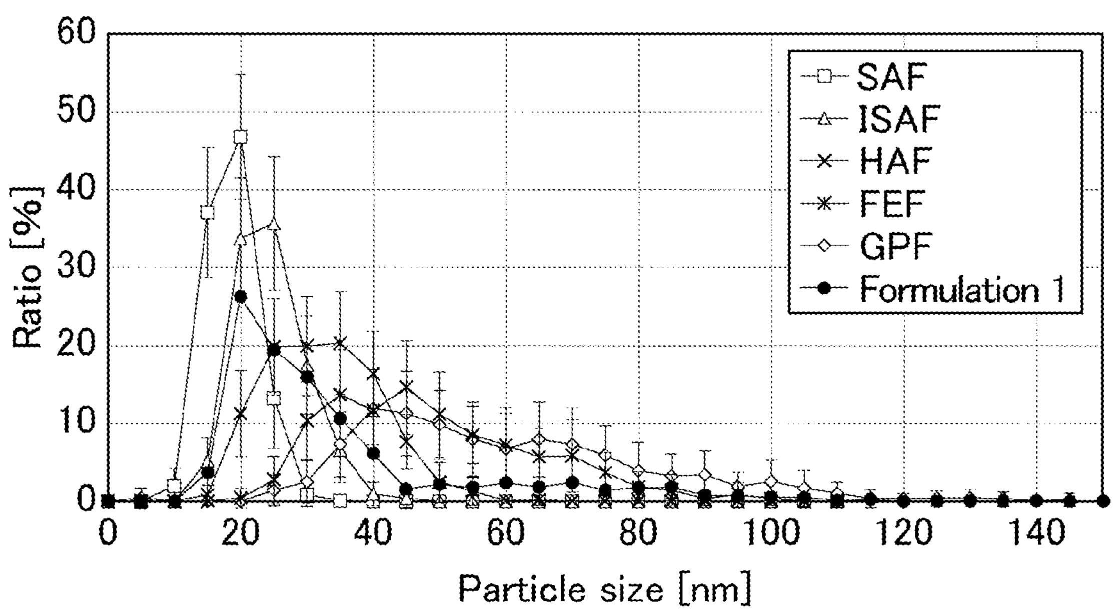

Here, the average particle sizes and particle size distributions (mean, LCL, UCL) of standard fillers (SAF, ISAF, HAF, FEF, GPF) were determined using a "Particle Analyzer LUZEX" (Nireco Corporation). FIGS. 1, 2, and 6 to also show the measurements.

Moreover, the means (average particle sizes) and standard deviations were determined from the obtained particle size distributions. Table 2 shows the values.

Preparation of Sample (Comparative Example)

The average particle sizes and particle size distribution widths of the samples (elastomer compositions) of Formulations 1 to 7 were determined using a "Particle Analyzer LUZEX" (Nireco Corporation). Table 1 shows the values.

TABLE 1

| Formulation table | | | | | | | | |
|---|---|---|---|---|---|---|---|---|
| | | Formulation 1 | Formulation 2 | Formulation 3 | Formulation 4 | Formulation 5 | Formulation 6 | Formulation 7 |
| Mixing ratio | ISAF | 80 | 66 | 50 | 33 | 20 | 100 | — |
| | GPF | 20 | 33 | 50 | 66 | 80 | — | 100 |
| Comparative Example | Average particle size (nm) | 31.7 | 33.7 | 40.0 | 46.0 | 50.8 | 20.7 | 58.0 |
| | Particle size distribution width (nm) | 19.4 | 19.3 | 22.3 | 22..8 | 22.2 | 4.4 | 19.0 |
| Example | Particle size distribution | FIG. 6 | FIG. 1 | FIG. 2 | FIG. 7 | FIG. 8 | FIG. 9 | FIG. 10 |

TABLE 2

| Average particle size and standard deviation of commercial products | | |
|---|---|---|
| Type of carbon black (name) | Average particle size (nm) | Standard deviation (nm) |
| SAF | 16.2 | 3.4 |
| ISAF | 22.0 | 6.0 |
| HAF | 30.0 | 8.3 |
| FEF | 46.2 | 16.6 |
| GPF | 57.5 | 21.7 |

Population (N1000)

Then, the same technique as described for FIGS. 1 to 5 was applied to the samples prepared in the example to estimate the types, amounts, and ratios of carbon black in Formulations 1 to 7. An estimation was made that the types, amounts, and ratios of carbon black in the samples were likely to be the types (ISAF, GPF), amounts, and ratios shown in Table 1.

In contrast, with respect to the comparative example, for example, the average particle size of carbon black in Formulation 4 was close to that of FEF, which failed to provide an estimation that the sample contained ISAF and GPF.

Exemplary embodiments of the present disclosure include:

Embodiment 1. An analysis method, including estimating a type, amount, and mixing ratio of at least one filler in an elastomer composition containing an elastomer component and the filler, the method including estimation based on a property, particle size, and particle size distribution of the filler.

Embodiment 2. The analysis method according to Embodiment 1, wherein the property of the filler is a shape of the filler.

Embodiment 3. The analysis method according to Embodiment 2, wherein the method includes estimating the type, amount, and mixing ratio of the filler in the elastomer composition based on a comparison between the shape, particle size, and particle size distribution of the filler and a shape, particle size, and particle size distribution of at least one standard filler obtained separately.

Embodiment 4. The analysis method according to any one of Embodiments 1 to 3, wherein the method includes treating the elastomer composition at a high temperature under a nitrogen atmosphere or air atmosphere, and analyzing the filler collected from the elastomer composition.

Embodiment 5. The analysis method according to Embodiment 4, wherein the treatment at a high temperature is carried out at 500 to 800° C.

Embodiment 6. The analysis method according to any one of Embodiments 1 to 5, wherein the property, particle size, and particle size distribution of the filler are obtained by electron microscopic observation.

Embodiment 7. The analysis method according to Embodiment 6, wherein the electron microscopic observation is transmission electron microscopic observation.

Embodiment 8. The analysis method according to Embodiment 6 or 7, wherein the shape, particle size, and particle size distribution of the filler are obtained based on electron microscopic images acquired by the electron microscopic observation.

Embodiment 9. The analysis method according to any one of Embodiments 1 to 8, wherein the filler is at least one of carbon black or silica.

The invention claimed is:

1. An analysis method comprising:

treating an elastomer composition comprising an elastomer component and fillers at a temperature in a range of 500° C. to 800° C. under a nitrogen atmosphere or air atmosphere to obtain a sample;

obtaining the shape, particle size, and particle size distribution of the fillers in the sample by using an electron microscope and analyzing electron microscopic images obtained by the electron microscope;

estimating a chemical grade, amount, and mixing ratio of the fillers in the sample, the estimation being based on the shape, particle size, and particle size distribution of the fillers in the sample, and a comparison between the shape, particle size, and particle size distribution of the fillers in the sample and a shape, particle size, and particle size distribution of respective reference fillers obtained separately;

estimating a number of chemical grades of each of the fillers in the sample based on a number of peaks in the particle size distribution of the respective fillers of the sample;

identifying the chemical grades of each of the fillers by dividing the particle size distribution of the respective filler contained in he sample into fixed sections and when a proportion of particle sizes within a section falls within a range between a lower control limit (LCL) and an upper control limit (UCL) of a corresponding section in a particle size distribution of the respective reference fillers, the filler is marked with the respective chemical grade, and calculating a match rate by dividing a number of marked sections by a total number of evaluated sections in the particle size distribution.

2. The analysis method according to claim 1, wherein a distribution width of the particle size distribution of the reference fillers is 5 nm or less.

3. The analysis method according to claim 1, wherein the particle size distribution is a mean particle size distribution.

4. The analysis method according to claim 1, further comprising comparing a peak height and a peak area of the particle size distribution of the fillers estimated to be present in the sample with those of the respective reference fillers, and calculating a content of each filler.

* * * * *